United States Patent
Long et al.

(10) Patent No.: US 10,482,192 B1
(45) Date of Patent: Nov. 19, 2019

(54) SYSTEMS AND METHODS FOR SELECTING AND MARKING A LOCATION ON A DENTAL ALIGNER

(71) Applicant: SmileDirectClub LLC, Nashville, TN (US)

(72) Inventors: Josh Long, Nashville, TN (US); Christopher Yancey, Nashville, TN (US); Tony Solarek, Nashville, TN (US); Clete Culp, Nashville, TN (US)

(73) Assignee: SmileDirectClub LLC, Nashville, TN (US)

( * ) Notice: Subject to any disclaimer, the term of this patent is extended or adjusted under 35 U.S.C. 154(b) by 0 days.

(21) Appl. No.: 16/273,893

(22) Filed: Feb. 12, 2019

(51) Int. Cl.
*G06F 17/50* (2006.01)
*A61C 7/00* (2006.01)
*A61C 7/08* (2006.01)

(52) U.S. Cl.
CPC ............ *G06F 17/50* (2013.01); *A61C 7/002* (2013.01); *A61C 7/08* (2013.01)

(58) Field of Classification Search
None
See application file for complete search history.

(56) References Cited

U.S. PATENT DOCUMENTS

| | | | |
|---|---|---|---|
| 3,688,963 A | 9/1972 | Snow et al. |
| 4,687,612 A | 8/1987 | Clarke et al. |
| 5,806,745 A | 9/1998 | Irwin |
| 5,975,893 A | 11/1999 | Chishti et al. |
| 6,350,120 B1 | 2/2002 | Sachdeva et al. |
| 6,371,761 B1 | 4/2002 | Cheang et al. |
| 6,398,548 B1 | 6/2002 | Muhammad et al. |
| 6,463,344 B1 | 10/2002 | Pavloskaia et al. |
| 6,633,789 B1 | 10/2003 | Nikolskiy et al. |
| 6,665,570 B2 | 12/2003 | Pavloskaia et al. |
| 6,688,886 B2 | 2/2004 | Hughes et al. |
| 6,776,614 B2 | 8/2004 | Wiechmann et al. |
| 6,918,761 B2 | 7/2005 | Sachdeva et al. |
| 6,976,627 B1 | 12/2005 | Culp et al. |

(Continued)

FOREIGN PATENT DOCUMENTS

EP 3091454 A1 * 11/2016 ......... G05B 19/4097

OTHER PUBLICATIONS

Lauren, Mark, and Fred McIntyre. "A new computer-assisted method for design and fabrication of occlusal splints." American Journal of Orthodontics and Dentofacial Orthopedics 133.4 (2008): S130-S135. (Year: 2008).*

(Continued)

*Primary Examiner* — Michelle M Entezari
(74) *Attorney, Agent, or Firm* — Foley & Lardner LLP

(57) ABSTRACT

Described herein are systems and methods for marking a dental aligner. A method for marking a dental aligner includes receiving a digital model corresponding to a dental aligner. The digital model includes a dental arch comprising a plurality of teeth. The method further includes determining whether a section of teeth on a right side or a left side of the dental arch includes flatter occlusal surfaces and selecting the section with the flatter occlusal surfaces, identifying surfaces on the teeth of the selected section that are flat relative to other surfaces on the teeth of the selected section, determining a line of best fit between the flat surfaces, and marking the dental aligner with a marking based on the line of best fit.

20 Claims, 6 Drawing Sheets

(56) References Cited

U.S. PATENT DOCUMENTS

| | | |
|---|---|---|
| 7,037,111 B2 | 5/2006 | Miller |
| 7,110,594 B2 | 9/2006 | Jones et al. |
| 7,261,533 B2 | 8/2007 | Wrosz et al. |
| 7,273,367 B2 | 9/2007 | Hughes et al. |
| 7,293,988 B2 | 11/2007 | Wen |
| 7,306,152 B2 | 12/2007 | Culp et al. |
| 7,309,230 B2 | 12/2007 | Wen |
| 7,319,529 B2 | 1/2008 | Babayoff |
| 7,333,874 B2 | 2/2008 | Taub et al. |
| 7,335,024 B2 | 2/2008 | Wen |
| 7,357,634 B2 | 4/2008 | Knopp |
| 7,361,018 B2 | 4/2008 | Imgrund et al. |
| 7,383,094 B2 | 6/2008 | Kopelman et al. |
| 7,384,266 B2 | 6/2008 | Wen |
| 7,433,810 B2 | 10/2008 | Pavloskaia et al. |
| 7,442,040 B2 | 10/2008 | Kuo |
| 7,476,100 B2 | 1/2009 | Kuo |
| 7,511,829 B2 | 3/2009 | Babayoff |
| 7,556,496 B2 | 7/2009 | Cinader et al. |
| 7,572,121 B2 | 8/2009 | Wrosz et al. |
| 7,578,673 B2 | 8/2009 | Wen et al. |
| 7,604,181 B2 | 10/2009 | Culp et al. |
| 7,611,058 B2 | 11/2009 | Culp et al. |
| 7,690,917 B2 | 4/2010 | Marshall |
| 7,695,278 B2 | 4/2010 | Sporbert et al. |
| 7,699,606 B2 | 4/2010 | Sachdeva et al. |
| 7,711,447 B2 | 5/2010 | Lu et al. |
| 7,738,989 B2 | 6/2010 | Taub et al. |
| 7,744,369 B2 | 6/2010 | Imgrund et al. |
| 7,831,322 B2 | 11/2010 | Liu et al. |
| 7,837,469 B2 | 11/2010 | Chishti et al. |
| 7,840,373 B2 | 11/2010 | Culp et al. |
| 7,865,259 B2 | 1/2011 | Kuo et al. |
| 7,905,408 B2 | 3/2011 | Culp et al. |
| 7,950,131 B2 | 5/2011 | Hilliard |
| 7,963,765 B2 | 6/2011 | Bergersen |
| 7,993,134 B2 | 8/2011 | Wen |
| 7,993,136 B2 | 8/2011 | Wen |
| 7,996,099 B2 | 8/2011 | Kopelman et al. |
| 8,029,277 B2 | 10/2011 | Imgrund et al. |
| 8,030,588 B2 | 10/2011 | Culp et al. |
| 8,038,444 B2 | 10/2011 | Kitching et al. |
| 8,047,846 B2 | 11/2011 | Wen |
| 8,060,236 B2 | 11/2011 | Hilliard |
| 8,075,306 B2 | 12/2011 | Kitching et al. |
| 8,083,976 B2 | 12/2011 | Lengsfeld et al. |
| 8,105,080 B2 | 1/2012 | Chishti et al. |
| 8,133,050 B2 | 3/2012 | Bergersen |
| 8,145,340 B2 | 3/2012 | Taub et al. |
| 8,155,780 B2 | 4/2012 | Lu et al. |
| 8,177,551 B2 | 5/2012 | Sachdeva et al. |
| 8,192,197 B2 | 6/2012 | Sporbert et al. |
| 8,199,988 B2 | 6/2012 | Marshall et al. |
| 8,244,390 B2 | 8/2012 | Kuo et al. |
| 8,296,952 B2 | 10/2012 | Greenberg |
| 8,301,287 B2 | 10/2012 | Kopelman et al. |
| 8,352,060 B2 | 1/2013 | Chun et al. |
| 8,383,977 B2 | 2/2013 | Culp et al. |
| 8,439,672 B2 | 5/2013 | Matov et al. |
| 8,451,456 B2 | 5/2013 | Babayoff |
| 8,469,706 B2 | 6/2013 | Kuo |
| 8,478,435 B2 | 7/2013 | Kuo et al. |
| 8,502,107 B2 | 8/2013 | Uckelmann |
| 8,562,338 B2 | 10/2013 | Kitching et al. |
| 8,562,340 B2 | 10/2013 | Chishti et al. |
| 8,587,582 B2 | 11/2013 | Matov et al. |
| 8,591,225 B2 | 11/2013 | Wu et al. |
| 8,636,510 B2 | 1/2014 | Kitching et al. |
| 8,684,729 B2 | 4/2014 | Wen |
| 8,738,165 B2 | 5/2014 | Cinader et al. |
| 8,740,614 B2 | 6/2014 | Wen et al. |
| 8,807,999 B2 | 8/2014 | Kuo et al. |
| 8,828,287 B2 | 9/2014 | Van Der Zel |
| 8,885,175 B2 | 11/2014 | Babayoff |
| 8,888,480 B2 | 11/2014 | Yoo et al. |
| 8,899,978 B2 | 12/2014 | Kitching et al. |
| 8,930,219 B2 | 1/2015 | Trosien et al. |
| 8,932,058 B2 | 1/2015 | Fisker et al. |
| 8,936,463 B2 | 1/2015 | Mason et al. |
| 9,011,149 B2 | 4/2015 | Wen |
| 9,017,072 B2 | 4/2015 | Kitching et al. |
| 9,069,914 B2 | 6/2015 | Kopelman et al. |
| 9,101,433 B2 | 8/2015 | Babayoff |
| 9,107,722 B2 | 8/2015 | Matov et al. |
| 9,108,338 B2 | 8/2015 | Sirovskiy et al. |
| 9,152,145 B2 | 10/2015 | Culp et al. |
| 9,161,823 B2 | 10/2015 | Morton et al. |
| 9,168,113 B2 | 10/2015 | Wu et al. |
| 9,183,764 B2 | 11/2015 | Sugimoto et al. |
| 9,192,305 B2 | 11/2015 | Levin |
| 9,241,774 B2 | 1/2016 | Li et al. |
| 9,326,830 B2 | 5/2016 | Kitching et al. |
| 9,330,205 B2 | 5/2016 | Lawitschka et al. |
| 9,333,052 B2 | 5/2016 | Miller |
| 9,364,297 B2 | 6/2016 | Kitching et al. |
| 9,393,083 B2 | 7/2016 | Bergersen |
| 9,403,238 B2 | 8/2016 | Culp |
| 9,404,740 B2 | 8/2016 | Babayoff |
| 9,414,897 B2 * | 8/2016 | Wu .............. A61C 7/002 |
| 9,433,477 B2 | 9/2016 | Borovinskih et al. |
| 9,433,479 B2 | 9/2016 | Phan et al. |
| 9,498,301 B2 | 11/2016 | Kim |
| 9,536,020 B2 | 1/2017 | Wen |
| 9,539,071 B2 | 1/2017 | Taub et al. |
| 9,566,132 B2 | 2/2017 | Stone-Collonge et al. |
| 9,572,637 B2 | 2/2017 | Jinkyun |
| 9,579,171 B2 | 2/2017 | Lorunser et al. |
| 9,597,164 B2 | 3/2017 | Li et al. |
| 9,610,140 B2 | 4/2017 | Anderson et al. |
| 9,622,834 B2 | 4/2017 | Chapoulaud et al. |
| 9,675,432 B2 | 6/2017 | Lee et al. |
| 9,717,568 B1 | 8/2017 | Adell |
| 9,717,573 B2 | 8/2017 | Vuillemot |
| 9,744,002 B2 | 8/2017 | Moss et al. |
| 9,763,750 B2 | 9/2017 | Kim et al. |
| 9,801,698 B2 | 10/2017 | Levin |
| 9,844,420 B2 | 12/2017 | Cheang |
| 9,844,429 B2 | 12/2017 | Kopelman et al. |
| 9,848,958 B2 | 12/2017 | Matov et al. |
| 9,861,452 B2 | 1/2018 | Rundlett |
| 9,861,457 B2 | 1/2018 | Fisker et al. |
| 9,888,982 B2 | 2/2018 | Lee |
| 9,922,170 B2 | 3/2018 | Trosien et al. |
| 9,937,023 B2 | 4/2018 | Andersson et al. |
| 9,939,258 B2 | 4/2018 | Lampert et al. |
| 9,943,382 B2 | 4/2018 | Wen |
| 9,956,058 B2 | 5/2018 | Kopelman |
| 9,962,238 B2 | 5/2018 | Boltunov et al. |
| 10,001,771 B2 | 6/2018 | Matty |
| 10,011,050 B2 | 7/2018 | Kitching et al. |
| 10,052,174 B2 | 8/2018 | Kitching et al. |
| 10,099,256 B2 | 10/2018 | Culp et al. |
| 10,109,114 B1 | 10/2018 | Yancey et al. |
| 10,111,730 B2 | 10/2018 | Webber et al. |
| 10,136,965 B2 | 11/2018 | Wiechmann et al. |
| 10,179,035 B2 | 1/2019 | Shivapuja et al. |
| 10,195,690 B2 | 2/2019 | Culp |
| 10,231,800 B2 | 3/2019 | Wiechmann |
| 10,238,472 B2 | 3/2019 | Levin |
| 10,241,499 B1 | 3/2019 | Griffin |
| 10,255,407 B2 | 4/2019 | Borovinskih et al. |
| 10,258,431 B2 | 4/2019 | Hong |
| 10,258,439 B1 | 4/2019 | Kitching et al. |
| 10,265,150 B2 | 4/2019 | Hultgren et al. |
| 10,271,923 B2 | 4/2019 | Kuo et al. |
| 10,278,794 B1 | 5/2019 | Raslambekov |
| 2003/0152884 A1 * | 8/2003 | Wiechmann .......... A61C 7/002 433/9 |
| 2004/0166456 A1 | 8/2004 | Chishti et al. |
| 2004/0243361 A1 | 12/2004 | Steuben et al. |
| 2006/0072810 A1 * | 4/2006 | Scharlack ............. G06K 9/00 382/154 |
| 2008/0187887 A1 | 8/2008 | Lu et al. |
| 2008/0300824 A1 | 12/2008 | Culp et al. |

(56) References Cited

U.S. PATENT DOCUMENTS

| | | |
|---|---|---|
| 2009/0061382 A1 | 3/2009 | Wen |
| 2010/0006640 A1 | 1/2010 | Culp et al. |
| 2011/0003025 A1 | 1/2011 | Patel |
| 2013/0073071 A1 | 3/2013 | Culp |
| 2013/0161241 A1 | 6/2013 | Culp et al. |
| 2015/0013688 A1 | 1/2015 | Frantz et al. |
| 2015/0250568 A1 | 9/2015 | Fisker et al. |
| 2015/0289960 A1* | 10/2015 | Shigemoto ........... A61B 5/1077 433/27 |
| 2015/0313687 A1 | 11/2015 | Blees et al. |
| 2015/0314520 A1 | 11/2015 | Sirovskiy et al. |
| 2016/0023249 A1 | 1/2016 | Culp et al. |
| 2016/0106572 A1 | 4/2016 | Frantz et al. |
| 2016/0206403 A1 | 7/2016 | Ouellette et al. |
| 2016/0242870 A1 | 8/2016 | Matov et al. |
| 2016/0310236 A1 | 10/2016 | Kopelman et al. |
| 2016/0332255 A1 | 11/2016 | Culp |
| 2016/0332367 A1 | 11/2016 | Sun et al. |
| 2017/0007359 A1 | 1/2017 | Kopelman et al. |
| 2017/0065373 A1 | 3/2017 | Martz et al. |
| 2017/0100207 A1 | 4/2017 | Wen |
| 2017/0112594 A1 | 4/2017 | Hilliard |
| 2017/0144360 A1 | 5/2017 | Moore et al. |
| 2017/0231721 A1 | 8/2017 | Akeel et al. |
| 2017/0281314 A1 | 10/2017 | Freimuller |
| 2017/0360535 A1 | 12/2017 | Rynerson et al. |
| 2017/0367792 A1 | 12/2017 | Raby et al. |
| 2018/0000564 A1 | 1/2018 | Cam et al. |
| 2018/0021106 A1 | 1/2018 | Khan |
| 2018/0036623 A1 | 2/2018 | Kuo |
| 2018/0055600 A1 | 3/2018 | Matov et al. |
| 2018/0071054 A1 | 3/2018 | Ha |
| 2018/0071062 A1 | 3/2018 | Kirchner et al. |
| 2018/0092713 A1 | 4/2018 | Boehlau et al. |
| 2018/0098828 A1 | 4/2018 | Hansen et al. |
| 2018/0116762 A1 | 5/2018 | Kopelman |
| 2018/0153651 A1 | 6/2018 | Tong et al. |
| 2018/0185118 A1 | 7/2018 | Sutter et al. |
| 2018/0235730 A1 | 8/2018 | Djamchidi |
| 2018/0263730 A1 | 9/2018 | Sirovskiy et al. |
| 2018/0271620 A1 | 9/2018 | Rodriguez et al. |
| 2018/0303581 A1 | 10/2018 | Martz et al. |
| 2018/0303582 A1 | 10/2018 | Hung |
| 2018/0318044 A1 | 11/2018 | Tal |
| 2018/0333224 A1 | 11/2018 | Van Esbroeck et al. |
| 2018/0333226 A1 | 11/2018 | Tsai et al. |
| 2018/0333231 A1 | 11/2018 | Somasundaram et al. |
| 2019/0019187 A1 | 1/2019 | Miller et al. |
| 2019/0029522 A1 | 1/2019 | Sato et al. |
| 2019/0029775 A1 | 1/2019 | Morton et al. |
| 2019/0039100 A1 | 2/2019 | Culp et al. |
| 2019/0053876 A1 | 2/2019 | Sterental et al. |
| 2019/0053883 A1 | 2/2019 | Sun et al. |
| 2019/0083208 A1 | 3/2019 | Hansen et al. |
| 2019/0090984 A1 | 3/2019 | Martz et al. |
| 2019/0125503 A1 | 5/2019 | Krolikowski et al. |
| 2019/0133716 A1 | 5/2019 | Kim et al. |
| 2019/0160590 A1 | 5/2019 | Culp |
| 2019/0164352 A1 | 5/2019 | Yancey et al. |
| 2019/0164353 A1 | 5/2019 | Yancey et al. |

OTHER PUBLICATIONS

EP 3091454 A1 [Machine translation] (Year: 2016).*
"Invisalign Manufacturing Process English" video, uploaded to YouTube on Apr. 7, 2014, https://www.youtube.com/watch?v=vsR0_wTR2a8.

* cited by examiner

SYSTEMS AND METHODS FOR SELECTING AND MARKING A LOCATION ON A DENTAL ALIGNER

BACKGROUND

The present invention relates generally to fabricating dental aligners. More specifically, the present disclosure relates to marking dental aligners.

A dental impression provides a negative imprint of the teeth and tissues in the mouth. The negative impression may then be utilized to produce a physical or digital reproduction of the teeth. Generally, a dental tray having a viscous, thixotropic impression material therein is fit over the dental arches of the patient. The impression material sets to a solid leaving an imprint of the dental structures in the mouth. When removed from the mouth, the impression provides a detailed and stable negative of the teeth. Optionally, the impression is processed using digital scanning methods to create the digital negative of the teeth.

Following a successful impression and generation of a positive mold or model of the dental impression, a vendor may generate a dental aligner from the positive mold of the dental impression. The vendor may generate dental aligners by thermoforming plastic to the positive mold. Oftentimes, such thermoforming is performed by an individual.

Fabrication of dental aligners may be done in a facility that produces dental aligners for many different patients. Additionally, realigning a patient's teeth using dental aligners may require using many different aligners for the same patient. As such, a facility may produce a large number of dental aligners, and tracking and organizing the aligners may be difficult.

SUMMARY

One embodiment relates to a method for marking a dental aligner. The method includes receiving a digital model corresponding to a dental aligner. The digital model includes a dental arch comprising a plurality of teeth. The method further includes determining whether a section of teeth on a right side or a left side of the dental arch includes flatter occlusal surfaces and selecting the section with the flatter occlusal surfaces, identifying surfaces on the teeth of the selected section that are flat relative to other surfaces on the teeth of the selected section, determining a line of best fit between the flat surfaces, and marking the dental aligner with a marking based on the line of best fit. As used herein, the terms "flat," "flattest," and the like are intended to mean any of surfaces that are flat, substantially flat, flatter than some of the other surfaces, flatter than most of the other surfaces, meeting or exceeding a threshold with respect to at least one other surfaces, etc.

Another embodiment relates to a system for marking a dental aligner. The system includes a processing circuit. The processing circuit includes at least one processor and a memory storing instructions. When executed by the at least one processor, the instructions cause the processing circuit to receive a digital model corresponding to a dental aligner. The digital model includes a dental arch comprising a plurality of teeth. The instructions further cause the processing circuit to determine whether a section of teeth on a right side or a left side of the dental arch includes flatter occlusal surfaces and select the section with the flatter occlusal surfaces, identify surfaces on the teeth of the selected section that are flat relative to other surfaces on the teeth of the selected section, and determine a line of best fit between the flat surfaces. The system further includes a marking system configured to mark the dental aligner with a marking based on the line of best fit.

Another embodiment relates to a memory storing instructions. When executed by a processor, the instructions cause a system to receive a digital model corresponding to a dental aligner. The digital model includes a dental arch comprising a plurality of teeth. The instructions further cause a system to determine whether a section of teeth on a right side or a left side of the dental arch includes flatter occlusal surfaces and select the section with the flatter occlusal surfaces, identify surfaces on the teeth of the selected section that are flat relative to other surfaces on the teeth of the selected section, determine a line of best fit between the flat surfaces, and provide the line of best fit to a marking system configured to mark the dental aligner with a marking based on the line of best fit.

DETAILED DESCRIPTION

Figure 1:
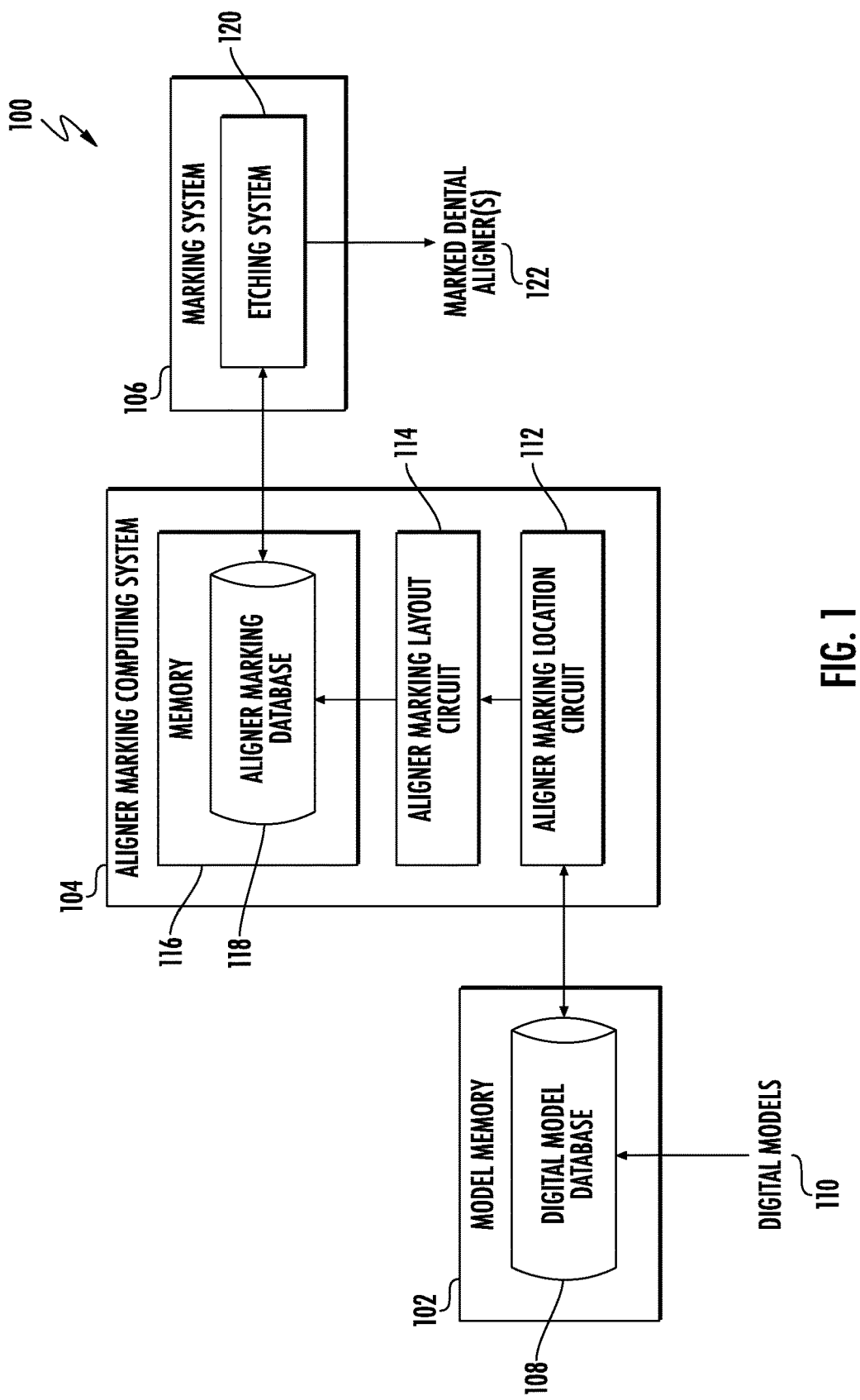
FIG. 1 is an illustration of a dental aligner marking system, according to an exemplary embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for marking digital aligners. In various embodiments, a system receives one or more digital models representing alignment positions for a patient's teeth. In one example, a patient or a dental professional creates an impression of the patient's teeth. The impression is then scanned to create a digital model of the patient's current teeth positions (e.g., an "initial digital model"). Alternatively, or additionally, a dental professional uses a scanning system to create the initial digital model. Once the initial digital model is created, the digital model is used to create a digital model representing the final aligned positions for the patient's teeth (e.g., a "final digital model"), and the final digital model is used to create one or more digital models representing one or more intermediate alignment positions that the patient's teeth will be guided through using dental aligners to reach the final aligned positions (e.g., "alignment digital model(s)").

Once the one or more alignment digital models have been created, a fabrication system is used to manufacture one or more physical models, each physical model corresponding to an alignment digital model or to the final digital model. For example, a three-dimensional ("3D") printing machine may be used to fabricate the one or more physical models. Dental aligners are then fabricated using the one or more physical models. In some embodiments, the dental aligners are produced by thermoforming plastic sheets over the physical model(s). Additionally, in some embodiments, multiple dental aligners are fabricated for each physical model. As an example, three dental aligners may be fabricated for each digital model, with each of the three dental aligners having a different rigidity (e.g., based on a hardness of the material used to fabricate the dental aligner or based on the thickness of the material used to fabricate the dental aligner). By wearing the dental aligners (e.g., in a predetermined sequence), the teeth of the patient are moved from their initial positions in the patient's mouth to the final positions modeled in the final digital model.

Facilities fabricating the dental aligners often fabricate large quantities of dental aligners at a given time. As such, to ensure that the right dental aligners are provided to the right patients, each dental aligner may be provided with a marking identifying the dental aligner. For example, a marking may identify the patient associated with the dental aligner and where the dental aligner fits into the predetermined sequence of tooth positions for the patient (e.g., in a treatment plan for the patient). As another example, each dental aligner may be assigned a marking that an individual may look up in a database to identify the patient and where the dental aligner fits into the predetermined sequence. Alternatively, a dental aligner may be marked to identify the dental aligner to a patient. As an example, a dental aligner may be marked to indicate to the patient which dental aligner in the predetermined sequence should be worn next. The process of determining the location of and creating these markings on dental aligners is described in further detail below.

Referring now to FIG. 1, an embodiment of a dental aligner marking system 100 is shown. As illustrated in FIG. 1, the system includes a model memory 102, an aligner marking computing system 104, and a marking system 106. The model memory 102, aligner marking computing system 104, and marking system 106 are operatively connected. In some embodiments, at least some of the model memory 102, aligner marking computing system 104, and marking system 106 may be connected via a network (e.g., the Internet, a wide-area network, a local area network, etc.). In other embodiments, alternatively or additionally, at least some of the model memory 102, aligner marking computing system 104, and marking system 106 may have a wired connection. Further, in some embodiments, at least some of the model memory 102, aligner marking computing system 104, and marking system 106 may be located in the same facility. In other embodiments at least some of the model memory 102, aligner marking computing system 104, and marking system 106 may be located in geographically separate facilities. As an example, the model memory 102 may be configured as a cloud storage system accessible by the aligner marking computing system 104 via the Internet, where the aligner marking computing system 104 is located in the same facility as the marking system 106. As another example, the aligner marking computing system 104 may be located in a first facility, and the marking system 106 may be located in a second facility. As such, the marking system 106 may retrieve instructions for marking dental aligners from the aligner marking computing system 104 via a network (e.g., via an internal file sharing program, via the Internet, etc.).

As shown in FIG. 1, the model memory 102 includes a digital model database 108. The digital model database 108 is configured to receive and retrievably store one or more digital models 110. For example, the digital model database 108 may receive the one or more digital models 110 from a separate computing system that created the digital model(s) 110. In some embodiments, the one or more digital models 110 stored in the digital model database 108 include the final digital model 110 and the alignment digital model(s) 110 for a given patient. In other embodiments, the one or more digital models stored in the digital model database 108 include one or more digital models used to fabricate the physical models. For example, the final and alignment digital models may be reformatted for 3D printing the physical models based on the final and alignment models, and these modified models may be saved in the digital model database 108.

The aligner marking computing system 104 includes an aligner marking location circuit 112. As shown, the aligner marking location circuit 112 is operatively connected to the digital model database 108 and is configured to retrieve digital models 110 from the digital model database 108. As an example, the digital model database 108 may store the digital models 110 in a sequential order (e.g., based on when the models were received, based on a patient's last name, etc.), and the aligner marking location circuit 112 may be configured to retrieve the digital models 110 in the sequential order. As another example, the aligner marking location circuit 112 may be configured to retrieve digital models 110 based on fabrication of the corresponding physical models (e.g., retrieve a digital model based on when the physical model corresponding to the digital model will be fabricated).

Once the aligner marking location circuit 112 has retrieved a given digital model, the aligner marking location circuit 112 is configured to determine a location for marking any aligners fabricated from a physical model corresponding to the digital model. For example, in some embodiments, the aligner marking location circuit 112 is configured to determine the location for marking the aligners by identifying a sequence of flat areas on occlusal surfaces of one side of the rear teeth, as described in further detail below with respect to FIG. 2.

The aligner marking computing system 104 also includes an aligner marking layout circuit 114 that is operatively connected to the aligner marking location circuit 112, as shown in FIG. 1. The aligner marking layout circuit 114 is configured to determine the layout of the marking at the aligner marking location(s) determined by the aligner marking location circuit 112. As an illustration, the aligner marking layout circuit 114 may determine how the marking fits at the aligner marking location(s). The marking may be, for example, a string of alphanumeric characters (e.g., a string of text). In some embodiments, the aligner marking layout circuit 114 is configured to generate the marking for the aligner. In other embodiments, the aligner marking layout circuit 114 is configured to receive the marking for the aligner, for example, from a centralized database assigning and storing the markings for aligners fabricated for a variety of patients. Further, in some embodiments, more than one dental aligner may be fabricated from the same physical model, as described above. In such embodiments, each dental aligner may include a different marking, and the aligner marking layout circuit 114 may accordingly be configured to determine the layout for each specific dental aligner. For example, the aligner marking layout circuit 114 can determine a layout from among a plurality of layout options (e.g., that vary the font, font size, characters, and/or formatting of the marking). Alternatively, in other embodiments, all dental aligners fabricated from a given physical model may include the same marking, and the aligner marking layout circuit 114 may instead generate one layout for all of the dental aligners corresponding to a given digital model.

As shown in FIG. 1, the aligner marking computing system 104 further includes a memory 116 including an aligner marking database 118. As further shown, the aligner marking database 118 is operatively connected to the aligner marking layout circuit 114. Accordingly, the aligner marking layout circuit 114 is configured to provide the aligner marking layout information (e.g., the layout of the marking for the dental aligner) to the aligner marking database 118, which retrievably stores the aligner marking layout information.

The marking system 106 includes an etching system 120. As shown in FIG. 1, the etching system 120 is operatively coupled to the memory 116 of the aligner marking computing system 104 and is configured to retrieve aligner marking layout information for a given aligner from the aligner marking database 118. The etching system 120 is further configured to use the aligner marking layout information to mark the corresponding fabricated dental aligner(s) with the marking according to the aligner marking layout information, producing marked dental aligner(s) 122. For example, the etching system 120 may include a laser that etches the marking into the fabricated dental aligner based on the layout determined by the aligner marking layout circuit 114. As another example, the etching system 120 may include a computer numeric control ("CNC") machine configured to etch the marking into the fabricated dental aligner based on the layout. Additionally, it should be understood that while the marking system 106 shown in FIG. 1 includes an etching system 120, in other embodiments, the marking system 106 may include another system for marking dental aligners, such as an ink printing system or a 3D printing system.

It should be understood that while the components of the system 100 are illustrated in the embodiment of FIG. 1 as being separate components, in some embodiments, one or more of the model memory 102, aligner marking computing system 104, and marking system 106 may be combined into the same device or system. For example, the aligner marking computing system 104 may be implemented as part of the marking system 106.

Figure 2:
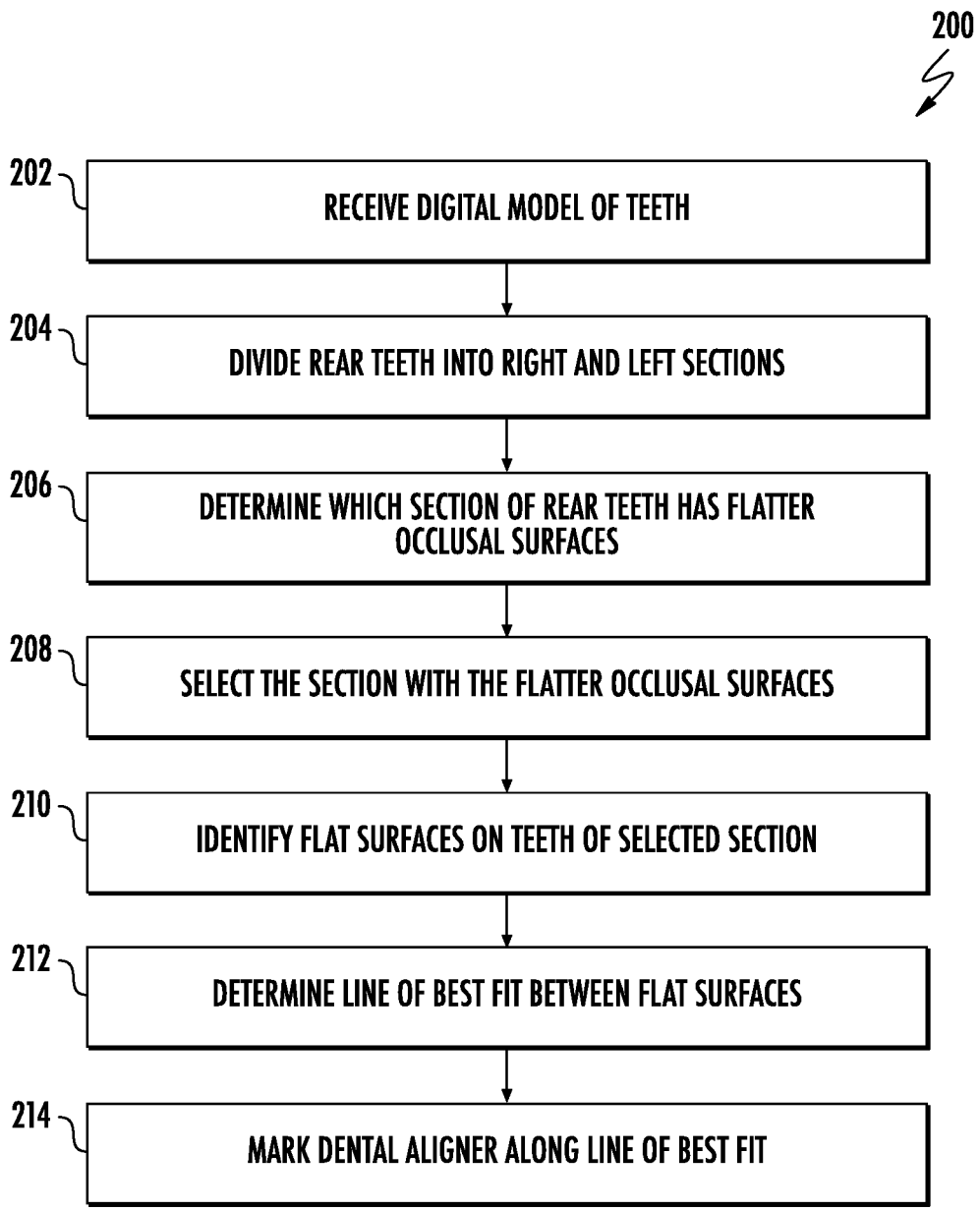
FIG. 2 is an illustration of a method of marking dental aligners, according to an exemplary embodiment.
Figure 3:
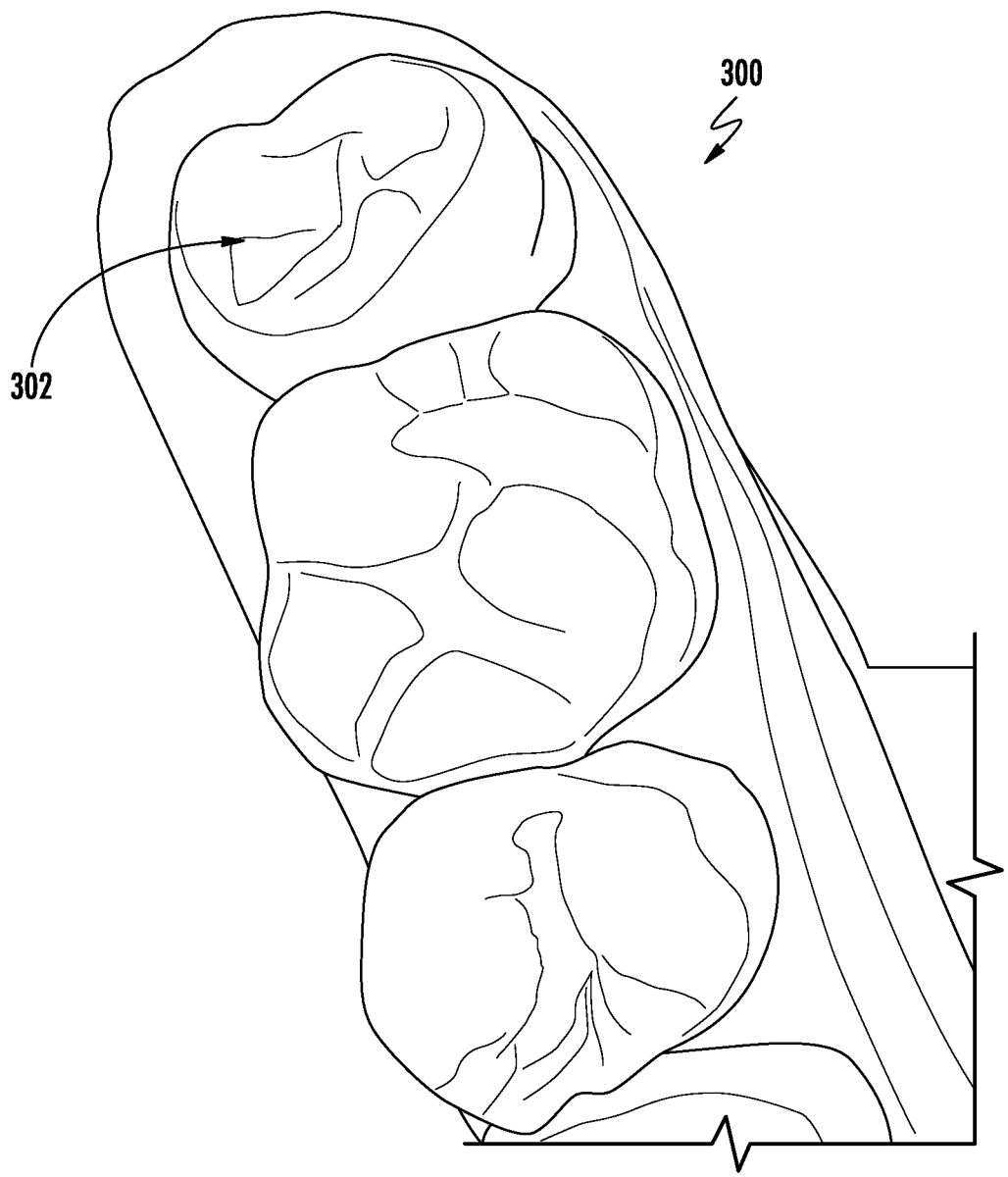
FIG. 3 is an illustration of a graphical user interface displaying a digital model of a patient's teeth, according to an exemplary embodiment.

Referring now to FIG. 2, an embodiment of a method 200 of marking dental aligners is illustrated. In various arrangements, the method 200 is implemented by the system 100 shown in FIG. 1, and as such, reference is made below to the components of the system 100 in describing the method 200. At operation 202, a digital model of a patient's teeth is received. As an illustration, FIG. 3 shows an example of a portion of a digital model 300, including the three rear teeth 302 on one side. In various embodiments, such as the digital model 300 in FIG. 3, the digital model corresponds to a physical model that has been or will be used to fabricate one or more dental aligners for the patient. For example, the digital model may be an alignment digital model representing an intermediate alignment of teeth positions for the patient's teeth or a final digital model representing final teeth positions for the patient's teeth.

Referring back to FIG. 2, at operation 204, the rear teeth of the digital model are divided into right and left sections. For example, a digital model may include a dental arch for a patient, including all of the patient's teeth. The teeth may be divided into right molars and premolars (e.g., teeth 5-8 or teeth 5-7 on the Palmer numbering system) and left molars and premolars. In another example, the digital model includes a dental arch that includes fewer than all of the patient's teeth such that it excludes the back-most molar or part of the back-most molar on each side of the dental arch.

At operation 206, the section of rear teeth having flatter occlusal surfaces is determined. As an example, in some embodiments, each tooth is represented in the digital model as a collection of polygons (e.g., triangle faces). Additionally, each digital model may be defined in x, y, and z-directions, where the z-direction is associated with the occlusal surfaces of the teeth. Accordingly, at operation 206, the aligner marking computing system 104 may determine a face normal vector for polygons viewable from the z direction, the face normal defined as a unit vector extending in the x, y, and z-directions and normal to the polygon face. Next, the aligner marking computing system 104 may determine the z component for each face normal vector, with the z component representing how flat its associated polygon is with respect to the z-direction (e.g., because a z-component closer to 1 means that the surface of the polygon is more perpendicular to the z-axis and is thus flatter). The aligner marking computing system 104 may then sum the z-components for all of the face normal vectors for each rear section of the teeth and divide the total by the number of polygon faces in the section to produce an average face normal z-component for that section. The section of rear teeth having an average face normal z-component closer to 1 is determined to have the flatter occlusal surfaces in the z-direction and, for example, have more markable surfaces than the teeth in the other section. As such, at operation 208, the section having the flatter occlusal surfaces is selected.

At operation 210, flat surfaces on the teeth of the selected section are identified. In some embodiments, identifying the flat surfaces includes determining whether the z-component for the face normal vector of each polygon making up the selected rear teeth is greater than or equal to a threshold value. For example, in some arrangements, the threshold value is 0.85. If the z-component for a given polygon's face normal vector is greater than or equal to the threshold value (e.g., 0.85), the aligner marking computing system 104 selects the polygon. Each group of selected contiguous polygons accordingly forms a flat surface of the selected rear teeth.

Figure 4:
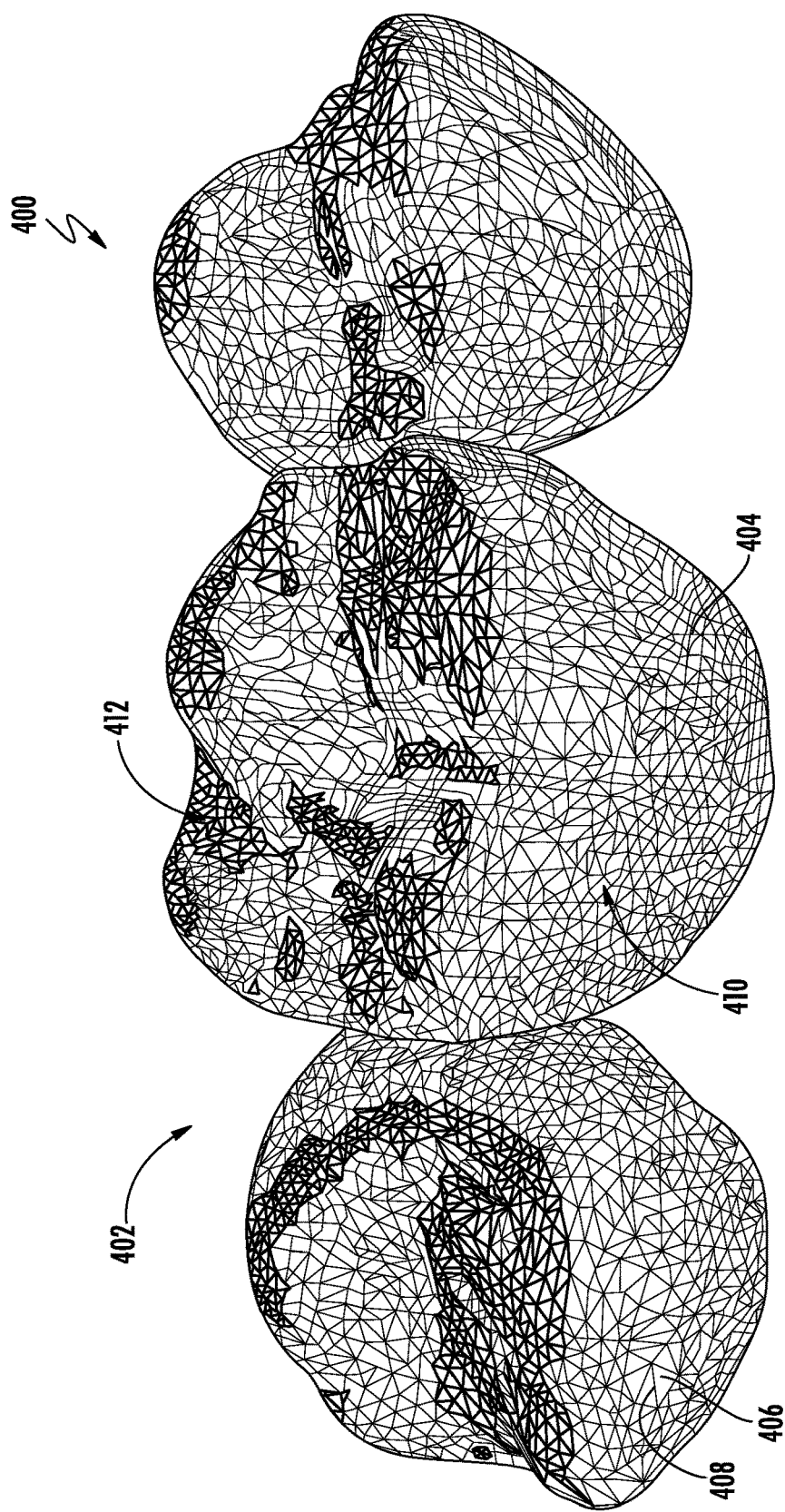
FIG. 4 is an illustration of a graphical user interface displaying a digital model of a patient's teeth and flat surfaces for marking a dental aligner, according to an exemplary embodiment.

As an example of the foregoing, FIG. 4 illustrates a graphical user interface 400 displaying flat surfaces on a digital model 402 of a patient's teeth 404 (e.g., the right or left rear three teeth), according to an exemplary embodiment. For example, the digital model 402 may show the teeth 404 determined to have flatter occlusal surfaces according to operations 206 and 208 of method 200, as described above. The digital model 402 is displayed in FIG. 4 such that the occlusal surfaces of the patient's teeth 404 are exposed. As shown in FIG. 4, the digital model 402 is formed from a large number of polygons 406, connected at edges 408. In the graphical user interface 400, a number of polygon 406 faces have been deselected (e.g., because the faces have face normal vectors with z components less than 0.85), creating deselected areas 410. Additionally, a number of polygon 406 faces have been selected (e.g., because the faces have face normal vectors with z components greater than or equal 0.85), creating flat surfaces 412 in the digital model 402.

Figure 5:
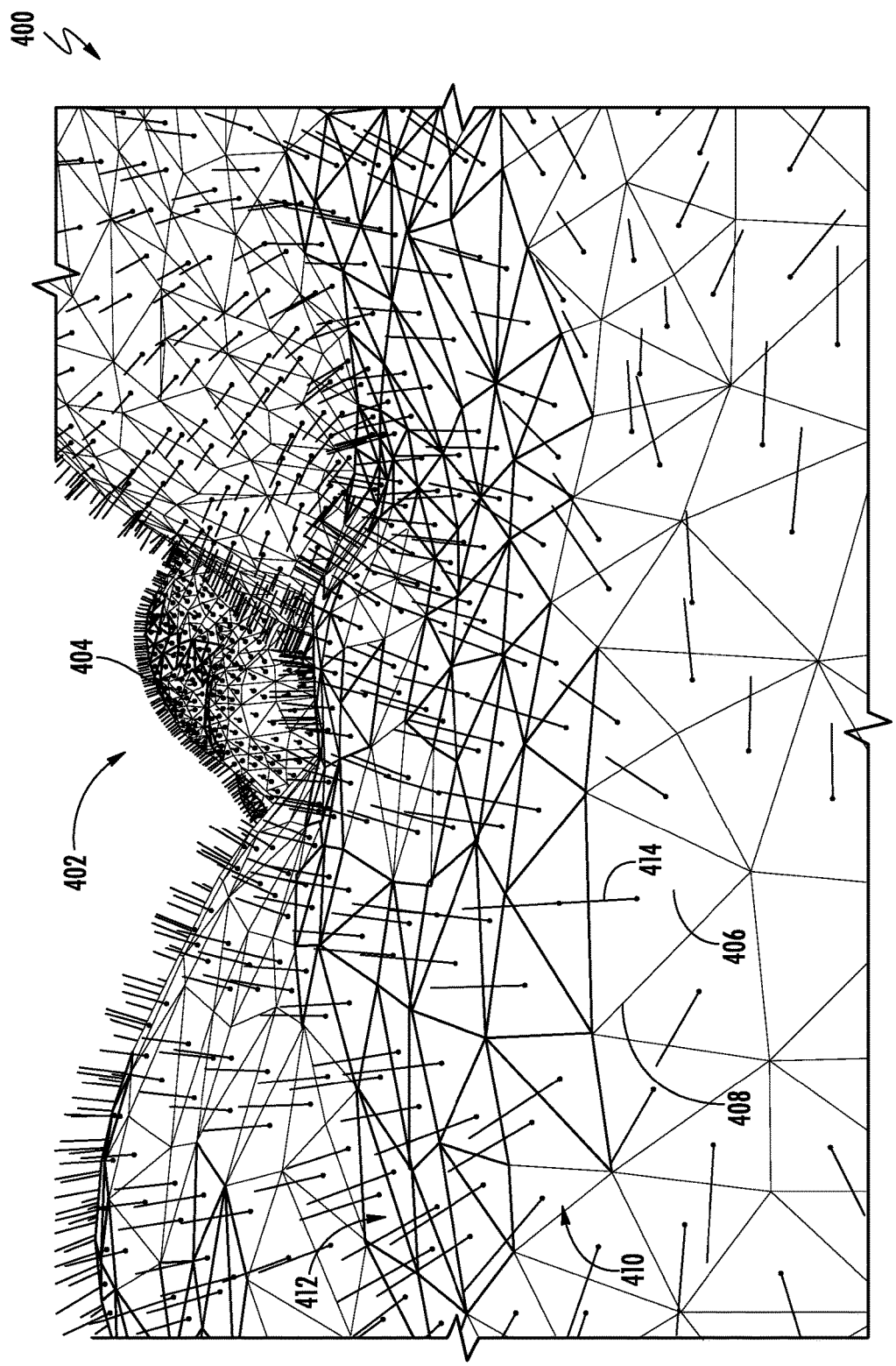
FIG. 5 is an illustration of the graphical user interface of FIG. 4 displaying the digital model and flat surfaces from another view, according to an exemplary embodiment.

More specifically, referring to FIG. 5, the graphical user interface 400 displaying the digital model 402 is shown from another view along the occlusal surfaces of the patient's teeth 404. As illustrated in FIG. 5, the model is formed from polygons 406 connected at edges 408. Additionally, a face normal 414 has been computed for each polygon 406, and these face normals 414 are also displayed in FIG. 5. The polygons 406 having a face normal 414 with a z component greater than or equal to the threshold value (e.g., 0.85) have been selected, with contiguous selected polygons 406 forming flat surfaces 412 in the digital model 402.

Referring back to FIG. 2, at operation 212, a line of best fit is determined between the flat surfaces. In some embodiments, once the flat surfaces have been selected for the rear teeth, the aligner marking computing system 104 determines a centroid (e.g., center average) for each flat surface. For example, an average of the x and y-components of the polygons making up the flat surface is taken to determine the centroid. A line of best fit is then drawn between the centroids (e.g., through at least three to five centroids of the flat surfaces). The best fit line represents a path that may be used in etching the marking on the dental aligner, as the best fit line defines a flat path, or "flattest path," (when viewed from the z-direction) along which the marking may be etched. In some embodiments, the line of best fit defining the potential etching path is up to 20 mm long, though it will be appreciated that a longer or shorter etching path may be used (e.g., a 30 mm long etching path, a 10 mm long etching path, etc.).

Figure 6:
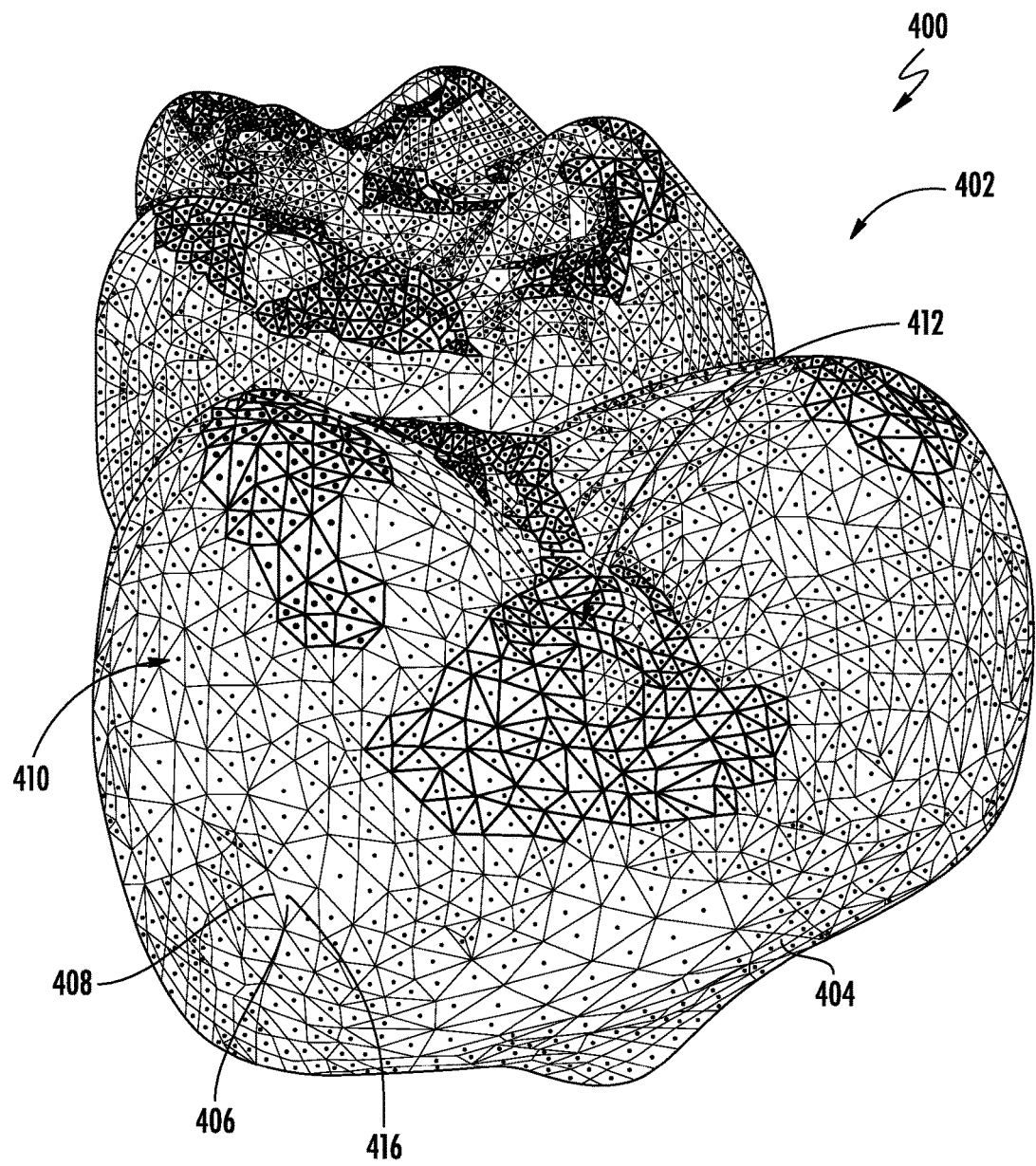
FIG. 6 is an illustration of the graphical user interface of FIG. 4 displaying the digital model and flat surfaces from another view, according to an exemplary embodiment.

For example, referring to FIG. 6, the graphical user interface 400 displaying the digital model 402 along the occlusal surfaces of the patient's teeth 404 is shown. As illustrated in FIG. 6, the center of each polygon 406 making up the digital model 402 (e.g., at which the face normal 414 is shown in FIG. 5) is displayed as a dot 416. The selected flat surfaces 412 of the digital model 402 are also displayed. Accordingly, at operation 212 of method 200, the centroid of each of these flat surfaces 412 may be calculated, and a best line may be fitted to these centroids to create the "flattest path" for marking the dental aligner corresponding to the digital model 402.

Referring back to FIG. 2, at operation 214, the dental aligner is marked along the line of best fit. For example, the marking is configured as a string of text that is etched along the best fit line using the marking system 106 (e.g., a laser etching system, CNC system, or other etching system). Accordingly, the aligner marking computing system 104 is configured to provide the best fit line to the marking system 106 for etching. In some arrangements, the text or other marking is configured such that the text fits along 7-12 mm of the etching path defined by the best fit line (e.g., extending along the first and part of the second tooth included in the rear teeth section).

Additionally, in some embodiments, operation 214 includes determining the layout of the marking along the line of best fit before the marking is etched. As an example, as described above, the aligner marking computing system 104 may determine how much of the marking (e.g., the text) will fit along a given flat surface included along the best fit line and, based on this determination, create a layout for the marking to be used when the dental aligner is etched. Furthermore, in some embodiments, multiple aligners may be fabricated from a single physical model corresponding to the digital model. As such, the aligner marking computing system 104 may determine or receive a separate marking for each dental aligner and determine a layout for each marking for its associated dental aligner before the dental aligner is etched. In some embodiments, a set of three dental aligners is fabricated from each physical model (e.g., hard, medium, and soft or thin, thicker, and thickest), and each of the aligners in the set is marked in the same location, while other sets of dental aligners for the same patient are marked in different locations.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with at least one general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps. It is important to note that the construction and arrangement of the systems and methods of marking dental aligners as shown in the various exemplary embodiments is illustrative only. Additionally, any element disclosed in one embodiment may be incorporated or utilized with any other embodiment disclosed herein. It should be appreciated that other elements of the various embodiments may be incorporated or utilized with any of the other embodiments disclosed herein.

What is claimed is:

1. A method for marking a dental aligner comprising:
   receiving a digital model corresponding to a dental aligner, the digital model including a dental arch comprising a plurality of teeth;
   determining whether a section of teeth on a right side or a left side of the dental arch includes flatter occlusal surfaces and selecting the section with the flatter occlusal surfaces;
   identifying surfaces on the teeth of the selected section that are flat relative to other surfaces on the teeth of the selected section;
   determining a line of best fit between the flat surfaces; and
   marking the dental aligner with a marking based on the line of best fit.

2. The method of claim 1, wherein the digital model comprises a plurality of polygons representing the occlusal surfaces of the teeth; and
   wherein determining whether the section of teeth on the right side or the left side of the dental arch includes flatter occlusal surfaces comprises determining whether the section of teeth on the right side or the left side of the dental arch includes flatter occlusal surfaces based on face normal vectors of the plurality of polygons.

3. The method of claim 2, wherein determining whether the section of teeth on the right side or the left side of the dental arch includes flatter occlusal surfaces and selecting the section with the flatter occlusal surfaces further comprises:
   determining a face normal vector for each polygon representing the occlusal surfaces in the digital model;
   determining a z-direction component for each face normal vector;
   determining an average z-direction component for each section of teeth; and
   selecting the section having the average z-direction component closer to 1.

4. The method of claim 1, wherein the digital model comprises a plurality of polygons representing the occlusal surfaces of the teeth, and wherein identifying the surfaces on the teeth of the selected section that are flat relative to other surfaces on the teeth of the selected section comprises:
   determining a face normal vector for each polygon representing the occlusal surfaces of the selected section in the digital model;
   determining a z-direction component for each face normal vector; and
   identifying each group of contiguous polygons having a face normal z-direction component greater than or equal to a threshold value as a flat surface.

5. The method of claim 4, wherein the threshold value is 0.85.

6. The method of claim 1, wherein determining the line of best fit between the flat surfaces comprises:
   determining a centroid for each flat surface; and
   determining the line of best fit between the centroids.

7. The method of claim 1, wherein marking the dental aligner based on the line of best fit comprises etching the dental aligner with the marking using a laser.

8. The method of claim 1, wherein the marking is a string of alphanumeric characters.

9. A system for marking a dental aligner comprising:
a processing circuit comprising at least one processor and a memory storing instructions that, when executed by the at least one processor, causes the processing circuit to:
receive a digital model corresponding to a dental aligner, the digital model including a dental arch comprising a plurality of teeth;
determine whether a section of teeth on a right side or a left side of the dental arch includes flatter occlusal surfaces and select the section with the flatter occlusal surfaces;
identify flat surfaces on the teeth of the selected section that are flat relative to other surfaces on the teeth of the selected section; and
determine a line of best fit between the flat surfaces; and
a marking system configured to mark the dental aligner with a marking based on the line of best fit.

10. The system of claim 9, wherein the digital model comprises a plurality of polygons representing the occlusal surfaces of the teeth; and
wherein the instructions cause the processing circuit to determine whether the section of teeth on the right side or the left side of the dental arch includes flatter occlusal surfaces based on face normal vectors of the plurality of polygons.

11. The system of claim 10, wherein the instructions further cause the processing circuit to determine whether the section of teeth on the right side or the left side of the dental arch includes flatter surfaces and select the section with the flatter occlusal surfaces by:
determining a face normal vector for each polygon representing the occlusal surfaces in the digital model;
determining a z-direction component for each face normal vector;
determining an average z-direction component for each section of teeth; and
selecting the section having the average z-direction component closer to 1.

12. The system of claim 9, wherein the digital model comprises a plurality of polygons representing the occlusal surfaces of the teeth, and wherein the instructions further cause the processing circuit to identify the surfaces on the teeth of the selected section that are flat relative to other surfaces on the teeth of the selected section by:
determining a face normal vector for each polygon representing the occlusal surfaces of the selected section in the digital model;
determining a z-direction component for each face normal vector; and
identifying each group of contiguous polygons having a face normal z-direction component greater than or equal to a threshold value as a flat surface.

13. The system of claim 12, wherein the threshold value is 0.85.

14. The system of claim 9, wherein the instructions further cause the processing circuit to determine the line of best fit between the flat surfaces by:
determining a centroid for each flat surface; and
determining the line of best fit between the centroids.

15. The system of claim 9, wherein the marking system is a laser etching system.

16. The system of claim 9, wherein the marking is a string of alphanumeric characters.

17. A memory storing instructions that, when executed by a processor, cause a system to:
receive a digital model corresponding to a dental aligner, the digital model including a dental arch comprising a plurality of teeth;
determine whether a section of teeth on a right side or a left side of the dental arch includes flatter occlusal surfaces and select the section with the flatter occlusal surfaces;
identify surfaces on the teeth of the selected section that are flat relative to other surfaces on the teeth of the selected section;
determine a line of best fit between the flat surfaces; and
provide the line of best fit to a marking system configured to mark the dental aligner with a marking based on the line of best fit.

18. The memory of claim 17, wherein the digital model comprises a plurality of polygons representing the occlusal surfaces of the teeth, and wherein the instructions further cause the system to determine whether the section of teeth on the right side or the left side of the dental arch includes flatter surfaces and select the section with the flatter occlusal surfaces by:
determining a face normal vector for each polygon representing the occlusal surfaces in the digital model;
determining a z-direction component for each face normal vector;
determining an average z-direction component for each section of teeth; and
selecting the section having the average z-direction component closer to 1.

19. The memory of claim 17, wherein the digital model comprises a plurality of polygons representing the occlusal surfaces of the teeth, and wherein the instructions further cause the system to identify the surfaces on the teeth of the selected section by:
determining a face normal vector for each polygon forming the occlusal surfaces of the selected section in the digital model;
determining a z-direction component for each face normal vector; and
identifying each group of contiguous polygons having a face normal z-direction component greater than or equal to a threshold value as a flat surface.

20. The memory of claim 17, wherein the instructions further cause the system to determine the line of best fit between the flat surfaces by:
determining a centroid for each flat surface; and
determining the line of best fit between the centroids.

* * * * *